US005535628A

United States Patent [19]
Rutherford

[11] Patent Number: 5,535,628
[45] Date of Patent: Jul. 16, 1996

[54] ULTRASONIC SCANNER HEAD AND METHOD

[75] Inventor: Jerry Rutherford, Anaheim, Calif.

[73] Assignee: Rohrback Cosasco Systems, Inc., Santa Fe Springs, Calif.

[21] Appl. No.: 358,332

[22] Filed: Nov. 14, 1994

[51] Int. Cl.⁶ .................................................. G01N 29/10
[52] U.S. Cl. .............................. 73/622; 73/629; 73/638; 73/640
[58] Field of Search ........................... 73/622, 620, 621, 73/629, 635, 638, 637, 640

[56] References Cited

U.S. PATENT DOCUMENTS

| | | | |
|---|---|---|---|
| 3,190,112 | 6/1965 | Beaujard et al. | 73/635 |
| 3,988,922 | 11/1976 | Clark et al. | 73/637 |
| 3,999,423 | 12/1976 | Tyree | 73/635 |
| 4,010,636 | 3/1977 | Clark et al. | 73/637 |
| 4,625,557 | 12/1986 | Rutherford | 73/635 |
| 4,774,842 | 10/1988 | Kollar et al. | 73/640 |
| 5,404,755 | 4/1995 | Olson et al. | 73/639 |

Primary Examiner—Hezron E. Williams
Assistant Examiner—Rose M. Finley
Attorney, Agent, or Firm—Renner, Otto, Boisselle & Sklar

[57] ABSTRACT

A scanner head for ultrasonic testing of structures includes a carriage with rollers supporting the carriage for movement over a surface being tested in a selected direction. A transverse frame is supported by the carriage and extends in a second direction crossing the one direction. A transducer is supported by the frame for movement along the frame to preset operative offset positions. For pipes or boiler tubes, the frame is in the form of an arc bar having a T-slot in which a holder for the transducer rides. With the carriage moving axially of the tube or pipe along a reference line, the arc bar keeps the transducer perpendicular to the surface regardless of the offset position. The rollers drive a distance increment signal generator to pulse the transducer and drive the ultrasonic transceiver and display circuitry.

27 Claims, 2 Drawing Sheets

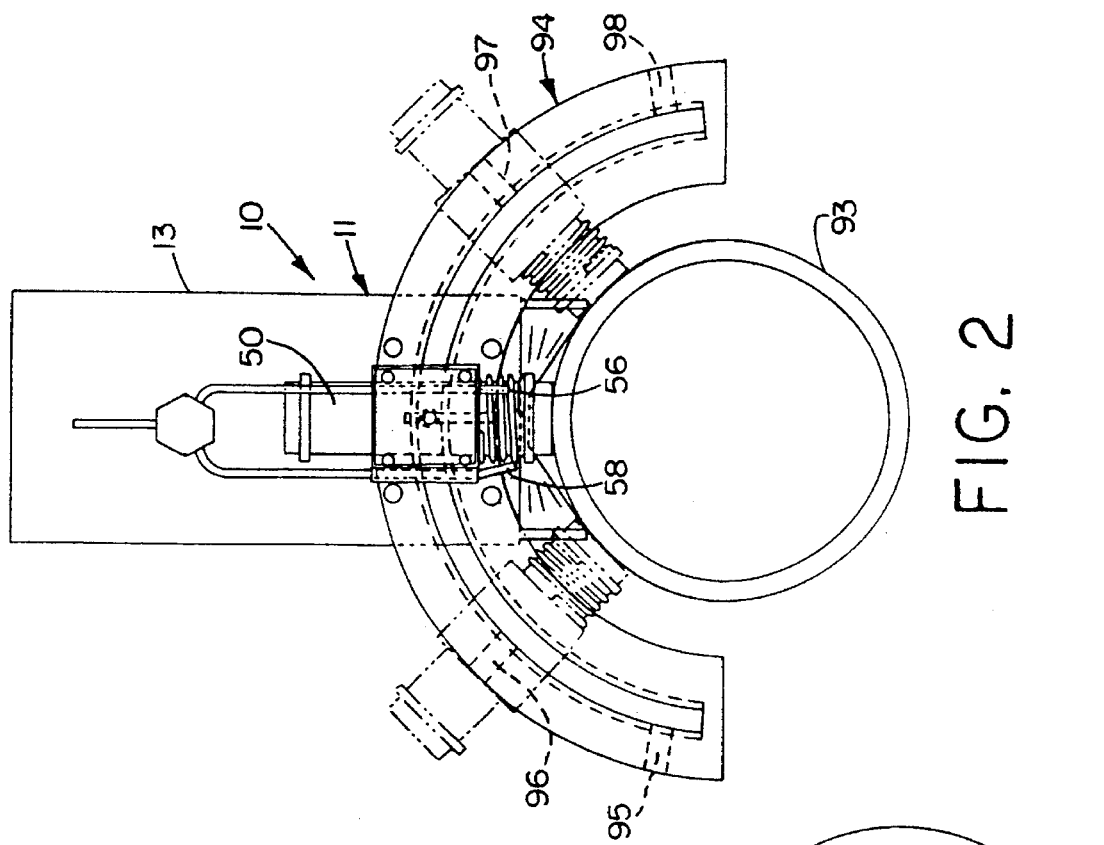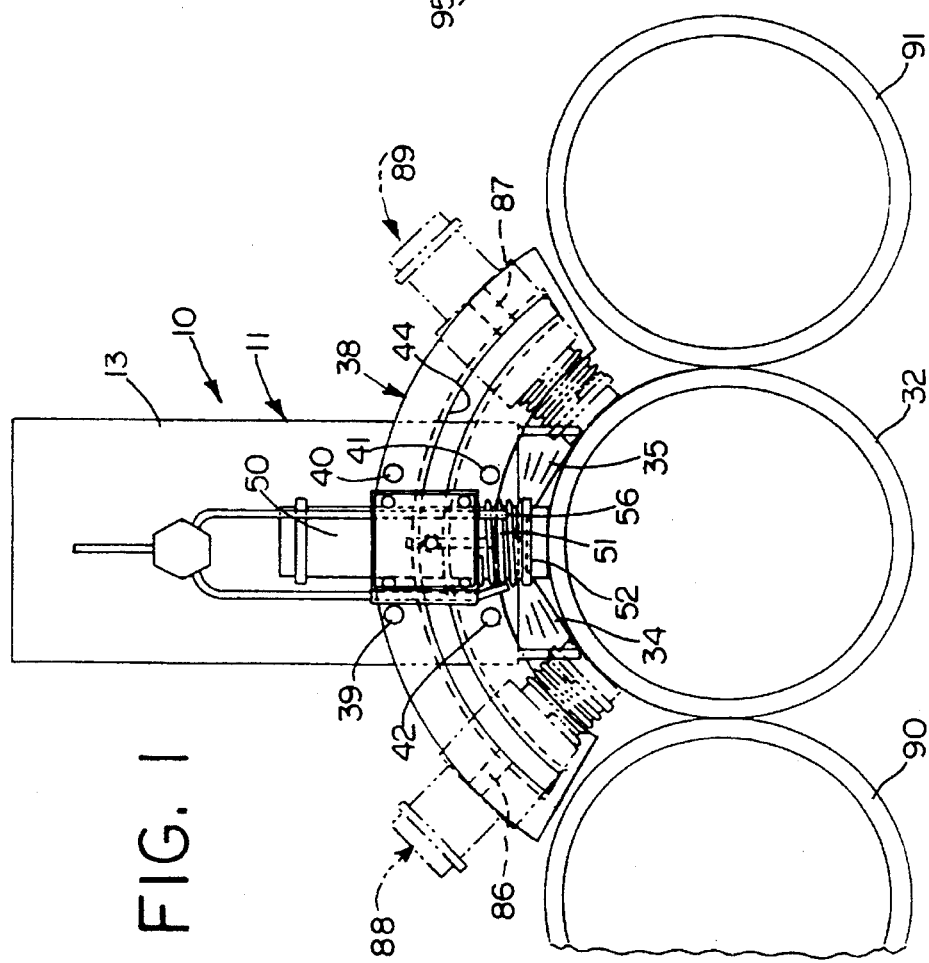

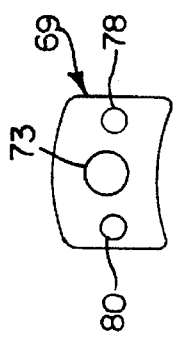
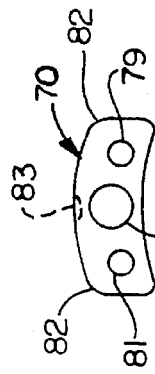
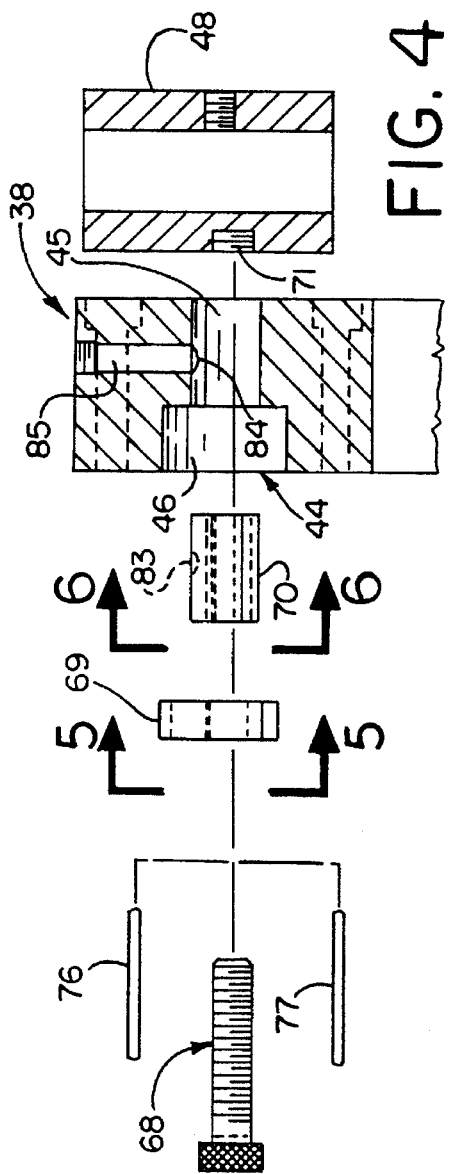
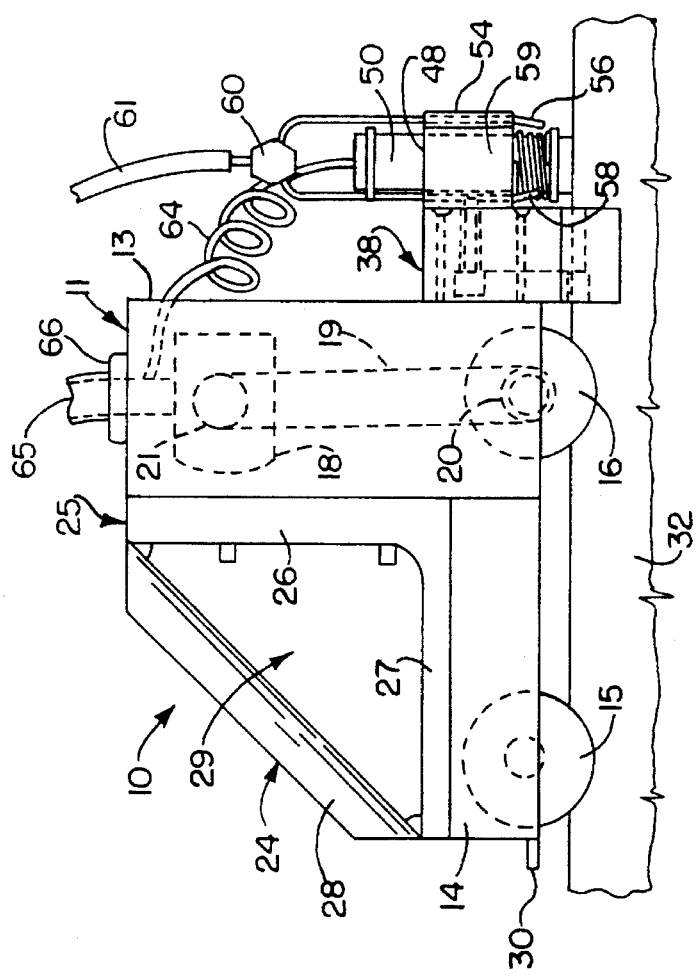

ULTRASONIC SCANNER HEAD AND METHOD

This invention relates generally as indicated to an ultrasonic scanner head and method, and more particularly to certain improvements in scanner head assemblies of the type seen in prior Rutherford U.S. Pat. No. 4,625,557, and also as seen in copending application for U.S. Letters Patent, Ser. No. 08/317,348, filed Oct. 4, 1994 and entitled "Scanner Head Assembly And Couplant System Therefore". The present invention also relates to a method of use of such hand held scanners to obtain more reliable and precise analytical results over time.

BACKGROUND OF THE INVENTION

A hand held scanner for an ultrasonic imaging system including a transducer is disclosed in U.S. Pat. No. 4,625,557. The scanner head includes a position encoder which provides distance increment signals as the scanner head is moved over a surface being analyzed. The position encoder is driven by a roller on the scanner head as the head is moved by hand over the surface. The position encoder drives the ultrasonic transceiver and display circuitry. The transceiver creates the pulse for the transducer. The transducer is thus pulsed from a distance increment signal. The scanner head is relatively small and may move in opposite directions on rollers in any direction.

The rollers include facing conical end sections which allow the curvature of a pipe or other surface to nest between such surfaces. The configuration of the rollers also allows the transducer to be nested between the rollers and the rollers positioned more closely together than would otherwise be the case. While the spacing of the rollers desirably enables the head to be quite small, approaching something on the order of an oversize stick of deodorant, it none-the-less makes the scanner head somewhat unstable. Even so, the scanner head may be randomly moved over a surface to generate an image showing thickness or defects in the structure. Also, while manipulating the scanner head, the operator may be watching the display and unattentive to the precise position of the scanner head and the location of the transducer on the surface being analyzed.

For a curved surface, the transducer should normally be aligned with the radius of curvature. For a pipe section the transducer should preferably always point to the center of the pipe. On planar or flat surfaces, the axis of the transducer should remain normal to the surface. With a small somewhat unstable head, care must be taken to keep the transducer in the proper position. Failure to keep the transducer in proper position may result in loss of couplant at the transducer-surface interface and the creation of air gaps. An angle variation will, in any event, affect the results obtained making them less reliable, and harder or impossible to repeat at a later date.

For many structures, proper repeatability is an important part of any ongoing analysis of corrosion or the development of possible defects. Many large structures such as process equipment or boilers are periodically taken out of service for maintenance and testing. For example, large boilers are routinely taken out of service after so many months of continuous operation. The periods of continuous operation may run a year or longer.

During such downtime, the boiler tubes, for example, may be ultrasonically tested for wall thickness or other defects. The results or images obtained are compared with the test results obtained the last time the structure was out of service. Accordingly, progressive changes can be monitored over the life of the equipment. If a meaningful comparison can not be made, then such a program has limited reliability. In order to have reliability, the testing should be done accurately and in a certain order at a known location, and then precisely repeated sometimes many months or even years later.

Accordingly, there is a need for a scanner having the advantages of a hand held scanner yet which has somewhat greater stability, and which can take measurements, reliably and repeatably at the same locations after lapses of substantial periods.

SUMMARY OF THE INVENTION

A hand held scanner has a carriage with a longer wheel base and is in the general form of an L with a diagonal handle connecting the ends of the two legs making the scanner easier to grip and hold in the desired location. The roller sets are along one leg of the L while the encoder driven by one set of rollers is housed in the other leg of the L. The handle is almost directly over the rollers providing fore and aft stability. The transducer is supported at the front of the carriage on a transverse frame which is arcuate in form for pipes, tubes or curved surfaces.

The transducer is indexable along the frame from a position in-line with the carriage and the direction of movement to an offset position. The frame includes a T-slot and the transducer is mounted through the slot by a T-shape projection or T-slider on the transducer holder. Detents enable the transducer to be positioned and repositioned at various locations offset from the center or in-line position. In this manner, the scanner may be moved along a single reference line repeatedly while the transducer is offset at one or a number of offset positions. The results are recorded including the offset and sequence and the testing can be repeated months or years later and a valid comparison made.

To the accomplishment of the foregoing and related ends the invention, then, comprises the features hereinafter fully described and particularly pointed out in the claims, the following description and the annexed drawings setting forth in detail certain illustrative embodiments of the invention, these being indicative, however, of but a few of the various ways in which the principles of the invention may be employed.

BRIEF DESCRIPTION OF THE DRAWINGS

FIG. 1 is an axial elevation of a scanner head in accordance with the present invention positioned on boiler tubes;

FIG. 2 is a similar view of a somewhat modified scanner head on a single pipe or tube;

FIG. 3 is a side elevation of the scanner head of FIGS. 1 or 2;

FIG. 4 is an exploded view of the arc bar/transducer holder connection;

FIG. 5 is an axial view of the T-cap as seen from the line 5—5 of FIG. 4; and

FIG. 6 is a similar view of the arc rider as seen from the line 6—6 of FIG. 4.

DETAILED DESCRIPTION OF THE PREFERRED EMBODIMENTS

Referring initially to FIGS. 1–3, there is illustrated a scanner head in accordance with the present invention shown generally at 10. The scanner head comprises a carriage shown generally at 11 which is in the general form of an L. This configuration of the carriage is seen more clearly in the elevation of FIG. 3. The carriage includes a vertical leg 13 in the form of a housing and a horizontal leg 14. Substantially spaced roller sets are provided at 15 and 16. The roller sets are along the horizontal portion or leg of the carriage. The roller set 16 drives encoder 18 through endless belt 19 and pulleys 20 and 21 on the roller and encoder, respectively.

The two legs of the L of the carriage are connected and reinforced by a handle shown generally at 24 in FIG. 3. The handle itself includes an L-shaped frame 25 which includes a vertical leg 26 and a horizontal leg 27 which are secured to the two parts of the carriage. Extending diagonally between the two legs 26 and 27 is a hand grip 28 to enable the scanner head to be readily hand held with the users fingers extending through the triangular opening 29. Projecting from the rear of the carriage leg 14 is a pointer 30 enabling the operator readily to line up the carriage with a reference line or other indicia on the structure 32 being tested. The handle extends diagonally over a substantial portion of the wheel base providing good fore and aft stability.

As seen more clearly in FIG. 1 and 2, the roller sets 15 and 16 have facing conical sections 34 and 35. The roller conical configurations are designed to permit the curved surface of the structure 32, shown in the form of a tube or pipe, to nest between the conical sections providing good lateral stability.

Secured to the front of the carriage is a transverse frame 38 which is in the form of an arcuate section of a curved bar having a same center of curvature as the structure 32. The transverse frame or bar 38 is secured to the front of the carriage by four fasteners indicated at 39, 40, 41 and 42, seen more clearly in FIG. 1. The transverse frame or arc bar includes an interior T-slot 44 running almost the arcuate length thereof. The configuration of this slot is seen more clearly in FIG. 4 and includes a relatively narrow portion 45 opening to the front of the bar and an enlarged head portion 46 opening to the rear of the bar.

Mounted on the arc bar for movement therealong is a transducer housing 48 supporting transducer 50 in a position radially aligned with the center of the pipe or structure 32. The transducer is urged downwardly or toward the structure by a compression spring 51 extending between the bottom of the housing and C-ring 52. A clamp plate 54 mounted on the front of the transducer housing 48 secures a couplant nozzle 56 in place. Another nozzle 58 is clamped to the side of the housing by clamp plate 59 almost diametrically opposite the nozzle 56. The nozzles are connected through hex fitting 60 to flexible hose 61 from the couplant source (not shown). The couplant will be supplied under pressure and through a control valve, as seen more clearly in the above noted copending application.

As can be seen in FIG. 3, the transducer 50 is electrically connected through the expansion cord 64 and the encoder is connected to the transceiver and the other components of the imaging system as indicated at 65 through strain relief 66. For the details of the other components of the ultrasonic imaging system, reference may be had to U.S. Pat. No. 4,625,557.

Referring now to FIG. 4, 5 and 6, it will be seen that the transducer housing 48 is mounted on the arc bar 38 by a fastener 68 which extends through T-cap 69, arc rider 70, and is threaded into blind tapped hole 71 in the transducer housing 48. The fastener is illustrated in the form of a knurled head cap screw which extends through untapped center holes 73 and 74 in the T-cap 69 and arc rider 70, respectively.

In order to keep the T-cap and arc rider from loosening and pivoting on the axis of fastener 68, there are also provided dowel pins 76 and 77. The dowel pin 76 extends through holes 78 and 79 in the T-cap and arc rider, respectively and into a blind hole, not shown, in the housing 48 with a force fit. Similarly, the dowel 77 extends through holes 80 and 81 in the T-cap and arc rider, respectively and into a blind hole in the transducer housing. When properly assembled, the T-cap and arc rider form a T-slider projection extending from the transducer housing securing the housing to the face of the arc bar while nonetheless permitting the housing to move arcuately along the bar while maintaining the housing in a radial position with respect to the center of the structure being tested.

It is noted that the top of the arc rider is provided with rounded top corners 82 and the top center of the arc rider is provided with a dimple or recess 83 which cooperates with the rounded projections 84 of spring loaded detents 85.

While the detent 85 is shown in the center of the arc bar in FIG. 4, holding the transducer 50 in the full line position seen in FIG. 1, it will also be appreciated that additional detents are provided at 86 and 87 seen at each end of the arc bar in FIG. 1 to secure the transducer holder and thus the transducer in the respective phantom line positions 88 and 89.

In comparing FIGS. 1 and 2, it will be seen that the arc T-bar in FIG. 1 extends approximately 120° and enables the transducer to be positioned in the center or at either of the phantom line positions 88 and 89. The configuration of the arc bar illustrated in FIG. 1 is designed to be used most beneficially in analyzing boiler tubes in large boiler structures. In such structures, the tubes 32 are positioned side-by-side as indicated at 90, 32 and 91. These boiler tubes form walls of large combustion chambers or fire boxes for steam generating plants and may be tested or analyzed from the exterior of the tube as shown.

The carriage may be moved along a reference line in the center of the tube with the transducer centered, and the results are obtained along that line. After the results are obtained, the transducer may be indexed to one end or the other of the arc T-bar and the scanner head is again simply moved along the reference line but with the transducer now in another location moving offset yet parallel to the carriage. Accordingly, with the embodiment of FIG. 1, it is possible to obtain the three different analytical paths for the transducer along the tube, each obtained while moving the carriage along the same reference line. To facilitate this movement along the reference line, the pointer 30 is provided.

Referring now to FIG. 2, it will be seen that the structure 93 is in the form of a pipe or tube which does not have adjacent pipes or tubes. In this manner, the arc bar 94 may be extended to surround the exterior of the pipe 93 by approximately 180°. The arc bar is provided with a detent location in the center for the full line position of the transducer 50 and also detent positions at 95, 96, 97 and 98, or 5 altogether. In this manner, the structure or pipe 93 may be analyzed or tested by moving the carriage 11 repeatedly along a reference line and between such movements the transducer is indexed to another position which is offset from the reference line. Accordingly, readings may be obtained along five different circumferentially offset paths even though the carriage is repeatedly moved along the same path. It will bee appreciated that additional detent locations and spacings may be provided.

The scanner head and method of the present invention provide much more precision than random hand held scanning. The scanner head also is more stable and ensures that the transducer is perpendicular or radially aligned with the surface at all times. The present invention thus provides a more regular search pattern, which, importantly, enables that pattern to be repeated months or even years later to obtain results for comparison over time.

The scanner head of the present invention thus enables the practice of a method of measuring the integrity of a metal structure with an ultrasonic scanning head which includes establishing a reference line on the structure, moving the scanning head and the transducer along the reference line to measure the integrity of the structure along such reference line. The transducer is then offset from the scanning head and the integrity of the structure is measured along the offset parallel path. The measurements, direction, and order of offset are recorded so that many months or years later the same measurements can be taken at the same locations so that the results may be compared over a substantial time.

Although the invention has been shown and described with respect to certain preferred embodiments, it is obvious that equivalent alterations and modifications will occur to others skilled in the art upon the reading and understanding of this specification. The present invention includes all such equivalent alterations and modifications, and is limited only by the scope of the claims.

What is claimed is:

1. A scanner head for the ultrasonic imaging from the exterior of structures having an arcuate surface having a center of curvature comprising a hand held carriage with supporting rollers adapted to engage the surface, said rollers being adapted to move said carriage along a reference line path on the surface, a transducer mounted on said carriage, means to adjust said transducer transversely of said path laterally to offset said transducer from said path, said means to adjust said transducer transversely comprising a frame on said carriage extending transversely of said path, and means to adjust the position of said transducer along said frame, said frame being arcuate and having substantially the same center of curvature as the structure.

2. A scanner head as set forth in claim 1 including a distance increment encoder for the transducer, and means driving said encoder from said rollers.

3. A scanner head as set forth in claim 1 including means to hold said transducer with respect to said frame at selected offset positions.

4. A scanner head as set forth in claim 1 including a couplant delivery system for said transducer, said delivery system moving with said transducer as said transducer is positionally adjusted along said frame.

5. A scanner head as set forth in claim 4 including a T-slot in said frame, and a T-slider in said slot supporting said transducer for movement therealong.

6. A scanner head as set forth in claim 5 including detent means in said frame at selected locations operative to engage said T-slider to hold said transducer in such selected locations.

7. A scanner head as set forth in claim 6 including two spaced rollers supporting said carriage, and a handle above the spaced rollers to provide fore and aft stability to the carriage.

8. A scanner head as set forth in claim 7 wherein said carriage is in the general form of an L, and said handle extends diagonally between the legs of the L.

9. A scanner head as set forth in claim 1 including means to maintain the transducer substantially perpendicular to the surface during movement of the carriage.

10. A scanner head for the ultrasonic imaging from an exterior surface of cylindrical structures having an axis, comprising a carriage including fore and aft spaced rollers for engaging the exterior surface of the structure and for moving the head in a linear direction axially along said exterior surface of the structure, a transducer mounted on said carriage ahead of said rollers, and means to adjust the position of said transducer generally transversely of said linear direction while maintaining the transducer directed substantially toward the axis in all positions of adjustment.

11. A scanner head as set forth in claim 10 including a handle above the spaced rollers to provide fore and aft stability to said carriage.

12. A scanner head as set forth in claim 10 wherein said means to adjust said transducer transversely comprises a frame extending transversely of said carriage supporting said transducer for transverse movement.

13. A scanner head for the ultrasonic imaging of structures from an exterior surface of the structure, comprising a carriage including fore and aft spaced rollers for engaging the exterior surface of the structure and for moving the head in a linear direction along said exterior surface of the structure, a transducer mounted on said carriage ahead of said rollers, means to adjust the position of said transducer generally transversely of said linear direction, and a handle above the spaced rollers to provide fore and aft stability to said carriage, said carriage being in the general form of an L with the rollers positioned along one leg of the L.

14. A scanner head as set forth in claim 13 wherein said handle extends diagonally between the legs of the L.

15. A scanner head as set forth in claim 14 including an incremental linear distance encoder pulsing the transducer, said encoder being positioned in the other leg of the L and driven by one of said rollers.

16. A scanner head for the ultrasonic imaging of structures from an exterior surface of the structure, comprising a carriage including fore and aft spaced rollers for engaging the exterior surface of the structure and for moving the head in a linear direction along said exterior surface of the structure, a transducer mounted on said carriage ahead of said rollers, and means to adjust the position of said transducer generally transversely of said linear direction, said means to adjust said transducer transversely comprising a T-slot bar frame extending transversely of said carriage supporting said transducer for transverse movement, and a T-slider extending through said slot and supporting said transducer for adjustment along said bar.

17. A scanner head as set forth in claim 16 including detent means in said frame at selected locations operative to engage said T-slider to hold said transducer in such selected locations.

18. A method of measuring the integrity of a metal structure with an ultrasonic scanning head which includes a carriage and transducer, establishing a reference line on the structure, moving the scanning head carriage and transducer along the reference line, measuring and recording the integrity of the structure along the reference line, offsetting the transducer from the reference line, measuring and recording the integrity of the structure along the offset by moving the carriage again along the reference line, recording the offset, repeating the measurements after a time period along the reference line and offset, and comparing the later measurements with the earlier measurements to determine any change in the integrity of the structure at the reference line and offset over the time period.

19. A method as set forth in claim 18 wherein the structure is cylindrical, and the reference line extends axially of the surface.

20. A method as set forth in claim 19 including the step of maintaining the transducer radially of the surface.

21. A method as set forth in claim 20 including the step of supplying couplant directly to the transducer at both the reference line and offset positions.

22. A method as set forth in claim 18 including the step of measuring the integrity of the structure at one or more offsets ,on each side of the reference line.

23. A method of measuring the integrity of a curved metal structure comprising the steps of creating a reference line on the exterior of the structure extending in a plane through the center of curvature of the structure, testing the integrity of the structure along the reference line, and along lines parallel to the reference line but angularly offset therefrom, recording the results, including the order and angular offset, then repeating the measurements and order of measurements after a lapse of a substantial period of time, recording the repeated measurements, and then comparing the earlier and repeated measurements to determine any change in the integrity of the structure over the substantial period of time.

24. A method as set forth in claim 23 wherein said metal structure is a pipe and the reference line extends parallel to the axis of the pipe.

25. A method as set forth in claim 23 wherein said structure is a boiler tube, and said reference line extends parallel to the axis of the tube.

26. A method as set forth in claim 23 wherein the testing steps are performed with a hand held ultrasonic scanning head including a transducer.

27. A method as set forth in claim 26 including the step of pulsing the transducer with distance increment signals as the transducer is moved along the reference line and offset parallel lines.

* * * * *